United States Patent [19]

Haber

[11] 4,381,311

[45] Apr. 26, 1983

[54] ANTIINFLAMMATORY 4,5-DIARYL-α-(POLYHALOMETHYL)-2-THIOPHENEMETHANOLS

[75] Inventor: Stephen B. Haber, Wilmington, Del.

[73] Assignee: E. I. Du Pont de Nemours and Company, Wilmington, Del.

[21] Appl. No.: 295,781

[22] Filed: Aug. 27, 1981

Related U.S. Application Data

[63] Continuation-in-part of Ser. No. 220,773, Dec. 29, 1980, abandoned.

[51] Int. Cl.$^3$ ............... A61K 31/38; A61K 31/44; C07D 333/16; C07D 401/00
[52] U.S. Cl. ............................... 424/275; 424/263; 549/75; 549/78; 549/79; 546/256; 546/268
[58] Field of Search ............... 549/75, 78, 79; 546/256, 268; 424/263, 275

[56] References Cited

U.S. PATENT DOCUMENTS

| | | | |
|---|---|---|---|
| 3,197,480 | 7/1965 | England | 260/326.5 |
| 3,531,497 | 9/1970 | Youngdale | 549/75 |
| 3,644,399 | 2/1972 | Brown | 549/78 |
| 3,652,575 | 3/1972 | Hutton et al. | 549/78 |
| 3,721,681 | 3/1973 | Hutton et al. | 548/78 |
| 4,174,405 | 11/1979 | Relyea | 549/78 |

OTHER PUBLICATIONS

Reinecke, et al., J. Chem. Soc., Chem. Commun. 585, (1980).

*Primary Examiner*—Alan Siegel

[57] ABSTRACT

4,5-Diaryl-α-(polyhalomethyl)-2-thiophenemethanols such as 4-(4-methoxyphenyl)-5-(4-methylthiophenyl)-α,α-bis(trifluoromethyl)-2-thiophenemethanol useful for treating arthritis and/or alleviating pain.

48 Claims, No Drawings

ANTIINFLAMMATORY 4,5-DIARYL-α-(POLYHALOMETHYL)-2-THIOPHENEMETHANOLS

RELATED APPLICATION

This application is a continuation-in-part of my copending application U.S. Ser. No. 220,773, filed Dec. 29, 1980, now abandoned.

BACKGROUND OF THE INVENTION

This invention relates to antiinflammatory diaryl thiophenes.

A number of references, such as *Compt. Rend.*, 242, 1738 (1956) and *Z. Chem.*, 13, 57 (1973), disclose the preparation of 2,3-diarylthiophenes.

M. G. Reinecke, et al., in *J. Chem. Soc., Chem. Commun.*, 585 (1980) disclose the gas phase thermolysis of 2,3-thiophenedicarboxylic anhydride in the presence of pentafluoroacetone and hexafluoroacetone followed by acidic hydrolysis to give 2-[α-difluoromethyl-α-(trifluoromethyl)hydroxymethyl]thiophene-3-carboxylic acid and 2-[α,α-bis(trifluoromethyl)hydroxymethyl]thiophene-3-carboxylic acid respectively. The latter was also prepared by lithiation of N,N-diethyl-3-thiophene carboxamide followed by reaction with hexafluoroacetone and acid hydrolysis. No biological activity is reported for any of these compounds.

D. C. England in U.S. Pat. No. 3,197,480 discloses α,α-bis(trifluoromethyl)pyrrole-2-methanol. Pharmaceutical use for the compounds of this patent is not disclosed.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side-effects. Many produce gastric irritation and other effects, such as changes in blood cells and central nervous system. Adrenocortical steroids produce gastric irritation and suppression of normal adrenal function.

The present invention results from efforts to develop new antiarthritic compounds with good antiinflammatory activity and minimal side effects that could be more effective in treating arthritis than presently available drugs.

In addition to antiinflammatory properties, some compounds of this invention have analgesic activity. This additional property is desirable in treatment of arthritis or related diseases; however, such compounds can be employed solely to alleviate pain.

SUMMARY OF THE INVENTION

This invention relates to novel antiinflammatory compounds of Formula I.

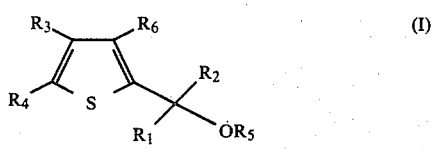

where $R_1$ and $R_2$ independently = $CF_3$, $CF_2H$, $CFCl_2$, $CF_2Cl$, $CClFH$, $CCl_2H$, $CH_2F$, $CF_3CF_2$ or $C_1$-$C_2$ alkyl with the provisos (1) that no more than one of $R_1$ and $R_2$ can be selected from the group consisting of $CH_2F$ and $C_1$-$C_2$ alkyl and (2) that no more than one of $R_1$ and $R_2$ can be $CF_3CF_2$;

$R_3$ and $R_4$ independently = pyridyl or

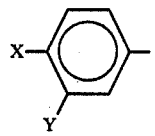

where

X=H, F, Cl, Br, $NO_2$, $C_1$-$C_2$ alkyl, $C_1$-$C_2$ alkoxy, di($C_1$-$C_2$ alkyl)amino or $C_1$-$C_2$ alkyl $S(O)_n$; where n=0, 1 or 2;

Y=H, F or Cl with the proviso that when Y is F or Cl, then X is F or Cl;

$R_5$=H, $C_1$-$C_4$ alkyl, ($C_1$-$C_3$ alkyl)C(O) or $CO_2R_7$;

$R_6$=H or $C_1$-$C_2$ alkyl; and $R_7$=$C_1$-$C_4$ alkyl.

Preferred compounds for utility considerations and/or ease of synthesis are where $R_5$ and $R_6$=H and:

(a) at least one of $R_1$ and $R_2$=$CF_3$ or $CF_2Cl$; or (b) $R_3$ and $R_4$ independently =

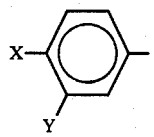

where

X=H, F, Cl, $CH_3O$, $(CH_3)_2N$, $CH_3S(O)_n$;

where n=0, 1 or 2; and

Y=H.

More preferred compounds are where: at least one of $R_1$ and $R_2$=$CF_3$ or $CF_2Cl$; and $R_3$ and $R_4$ independently =

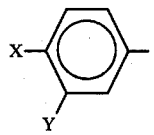

where

X=H, F, Cl, $CH_3S$ or $CH_3O$; and

Y=H; and $R_5$ and $R_6$=H.

Most preferred compounds are where $R_5$ and $R_6$=H and:

(a) one of $R_1$ and $R_2$=$CF_3$ or $CF_2Cl$ and the other=$CH_3$, $CF_2Cl$ or $CF_3$; or (b) $R_3$ and $R_4$ independently =

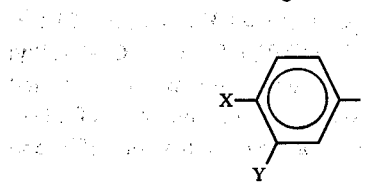

where
X=F, Cl or CH$_3$S; and
Y=H.

Specifically preferred compounds are:
4-(4-Methoxyphenyl)-5-(4-methylthiophenyl)-α,α-bis(-trifluoromethyl)-2-thiophenemethanol;
4,5-Bis(4-fluorophenyl)-α-methyl-α-trifluoromethyl-2-thiophenemethanol;
4,5-Bis(4-fluorophenyl)-α,α-bis(trifluoromethyl)-2-thiophenemethanol;
5-(4-Chlorophenyl)-4-(4-fluorophenyl)-α,α-bis(trifluoromethyl)-2-thiophenemethanol;
4,5-Bis(4-fluorophenyl)-α,α-bis(chlorodifluoromethyl)-2-thiophenemethanol; and
4,5-Bis(4-fluorophenyl)-α-chlorodifluoromethyl-α-trifluoromethyl-2-thiophenemethanol.

SYNTHESIS

The compounds of the invention may be prepared by the following reactions:

Method A

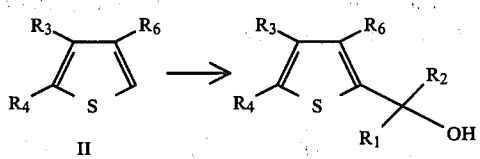

A 2,3-diarylthiophene II is reacted with a strong base such as n-butyl lithium or t-butyl lithium in a solvent such as tetrahydrofuran, toluene or diethyl ether, optionally in the presence of a complexing agent such as tetramethylethylenediamine and then treated with a halogenated ketone to give a compound of Formula I where R$_5$=H. The reaction can be carried out at a temperature from −78° to 110° C.

Method B

A 2,3-diarylthiophene II in an inert solvent such as toluene in the presence of an acidic catalyst, e.g., trifluoroacetic acid, stannic chloride or aluminum chloride, is reacted with a halogenated ketone or its hydrate to give a compound of Formula I where R$_5$=H.

Method C

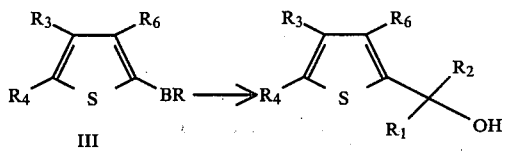

A 2-bromo-4,5-diarylthiophene III is treated with a strong base such as n-butyl lithium or t-butyl lithium in a solvent such as tetrahydrofuran, ether or toluene optionally in the presence of a complexing agent such as tetramethylethylenediamine at a temperature from −78° to 40° C., preferably at −30° to 30° C. The resultant lithio thiophene is treated with a halogenated ketone at a temperature from −78° to 40° C. to give a compound of Formula I where R$_5$=H.

2-Bromo-4,5-diarylthiophenes III are prepared by the reaction of a 2,3-diarylthiophene II with bromine (1 equivalent) in a solvent such as methylene chloride, acetic acid or their mixture at a temperature from −20° to 30° C.

Method D

A 2-bromo-4,5-diarylthiophene III is reacted with magnesium in a solvent such as ether or tetrahydrofuran at a temperature from 0° to 65° C. to form the corresponding Grignard reagent and then treated with a halogenated ketone at a temperature from −78° to 65° C. to give a compound of Formula I where R$_5$=H.

Method E

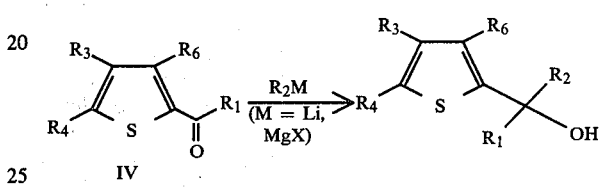

A 2-acyl-4,5-diarylthiophene is treated with an alkyl lithium or alkyl Grignard reagent in a solvent such as diethyl ether or tetrahydrofuran at a temperature from −78° to the boiling point of the solvent, preferably at 0° to 30° C., to give a compound of Formula I where R$_5$=H.

2-Acyl-4,5-diarylthiophenes may be prepared by the reaction of a 2-lithio-4,5-diarylthiophene or a 2-(4,5-diarylthienyl)magnesium halide with a suitable derivative of the carboxylic acid corresponding to the desired acyl moiety. Suitable derivatives include anhydrides, esters, acid halides and amides. The reaction may be carried out in a solvent such as diethyl ether or tetrahydrofuran at a temperature from −78° to the boiling point of the solvent, preferably at −78° to 0° C.

Alternatively, reaction of a 4,5-diarylthiophene with an acid anhydride in the presence of an acid catalyst in a solvent such as chloroform or methylene chloride produces a 2-acyl-4,5-diarylthiophene. The reaction may be performed at a temperature from 20° to the boiling point of the solvent.

Method F (R'$_6$ = C$_1$-C$_2$ alkyl)

A dibromothiophene of structure V in a solvent such as diethyl ether or tetrahydrofuran at a temperature from −78° to 35° C. is metallated with a reagent such as n-butyl lithium or magnesium and then treated with a halogenated ketone. The resultant intermediate is further treated with a reagent such as n-butyl lithium or magnesium and then with an alkylating agent to give a compound of Formula I where R$_5$=H.

2,3-Dibromo-4,5-diarylthiophenes V are prepared by reaction of a 2,3-diarylthiophene II (R$_6$=H) with bromine (2 equivalents) in a solvent mixture such as methylene chloride and acetic acid at a temperature from 0° to 55° C.

Method G

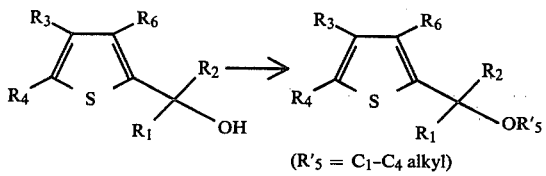

(R'₅ = C₁-C₄ alkyl)

A compound of Formula I ($R_5$=H) in a solvent such as acetone or dimethylformamide is treated with an alkylating agent in the presence of a base such as potassium carbonate, pyridine, triethylamine, potassium t-butoxide or sodium hydride to give a compound of Formula I.

Method H

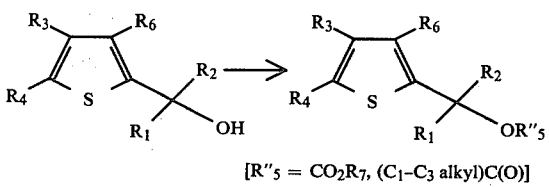

[R"₅ = CO₂R₇, (C₁-C₃ alkyl)C(O)]

A compound of Formula I ($R_5$=H) is treated with a base and then an acid chloride to give a compound of Formula I. Alternatively, direct reaction of a compound of Formula I ($R_5$=H) with an acid anhydride gives a compound of Formula I.

The compounds of the invention and their synthesis are illustrated further by the following examples. All temperatures are in degrees Centigrade.

EXAMPLE 1

4,5-Bis(4-fluorophenyl)-α,α-bis(trifluoromethyl)-2-thiophenemethanol

Method A 2,3-Bis(4-fluorophenyl)thiophene (4.08 g, 15 mmoles) was dissolved in 100 ml toluene and the volume reduced by approximately half by distillation. The cooled solution was diluted with 150 ml diethyl ether, cooled to ~5° and treated with 1.6 M n-butyl lithium (12 ml, 19.2 mmole). The reaction mixture was heated at reflux for 1.5 hours, cooled to −78° and treated with hexafluoroacetone (2.5 ml, ~1.5 equivalents) as a gas. The reaction mixture was stirred at −78° for 45 minutes and then allowed to warm to room temperature.

The reaction mixture was stirred overnight at room temperature, purged with N₂ and quenched with 1 N HCl. The aqueous phase was extracted with ethyl acetate and the combined organics washed with brine, dried and concentrated on the rotary evaporator. Chromatography on silica gel and crystallization from hexanes gave the title compound (1.7 g), m.p. 75°-8°. Infrared and proton NMR spectra were consistent with the assigned structure. MS 438 (M+), 369 (M—CF₃).

Anal. Calcd. for C₁₉H₁₀F₈OS: C, 52.06; H, 2.30; Found: C, 52.34; H, 2.26.

Method B

A solution of 2,3-bis(4-fluorophenyl)thiophene (3.4 g, 12.5 mmoles) in 50 ml toluene was treated with trifluoroacetic acid (15 ml) and then hexafluoroacetone trihydrate (3.1 ml, ~1.1 equivalents) and heated at reflux for 31 hours. An additional portion of hexafluoroacetone trihydrate (3 ml) was added and heating continued for 48 hours.

The reaction mixture was concentrated in vacuo. The residue was dissolved in ethyl acetate, washed twice with water, once with saturated aqueous NaHCO₃, once with brine, dried and concentrated on a rotary evaporator. TLC analysis showed a mixture (~1:1) of starting material and a more polar product.

This mixture was dissolved in 100 ml toluene, treated with hexafluoroacetone trihydrate (2 ml) and aluminum chloride (220 mg) and then heated at reflux for 24 hours. An additional portion of aluminum chloride (200 mg) was added and heating continued for 72 hours.

The reaction mixture was concentrated in vacuo. The residue was dissolved in ethyl acetate, washed with 1 N HCl and brine, dried and concentrated on the rotary evaporator. Chromatography on silica gel gave a solid which was identified by mass spectroscopy and TLC behavior to be predominantly the title compound.

EXAMPLE 2

Method C a. 2-Bromo-4,5-bis(4-fluorophenyl)thiophene

A solution of 2,3-bis(4-fluorophenyl)thiophene (272 mg, 1 mmole) in 3 ml methylene chloride was diluted with 3 ml glacial acetic acid and cooled to 10°. A solution of 0.5 M bromine in acetic acid (1.1 ml) was added. After 2½ hours an additional portion of bromine in acetic acid (1.1 ml) was added. After a total rection time of 5½ hours, the reaction mixture was concentrated in vacuo.

The residue was dissolved in ethyl acetate, washed with saturated aqueous NaHCO₃ and brine, dried and concentrated on the rotary evaporator. Recrystallization from methanol gave the title compound (145 mg), m.p. 86°-89°. MS 350,352 (M+).

b. 4,5-Bis(4-fluorophenyl)-α-(chlorodifluoromethyl)-α-dichlorofluoromethyl)-2-thiophenemethanol A solution of 2-bromo-4,5-bis(4-fluorophenyl)thiophene (4.38 g, 12.5 mmoles) in 100 ml tetrahydrofuran was cooled to −5° and treated dropwise with 1.6 M n-butyl lithium (10 ml, 1.3 equivalents). The reaction mixture was stirred for 45 minutes at −5°, cooled to −55° and treated dropwise with a solution of 1,1,3-trichlorotrifluoroacetone (3.8 g, 1.4 equivalents) in 5 ml tetrahydrofuran. The reaction mixture was stirred for 1 hour at −50° and then allowed to warm to room temperature overnight.

The reaction mixture was quenched with 1 N HCl and the aqueous phase extracted with ethyl acetate. The combined organics were washed with saturated aqueous NaHCO₃ and brine, dried and concentrated on the rotary evaporator. Chromatography on silica gel gave the title compound as an oil (0.6 g).

¹⁹F nmr: −59.55 and −59.64 ppm (2d, J=17 Hz) (CF₂Cl); −63.15 (t, J=17 Hz) (CFCl₂), −113.35 (s)(F-phenyl), −114.90 (s), (F-phenyl).

Using the appropriate halogenated ketone, the following compounds can be prepared following the procedures outlined above and illustrated in the preceding examples.

TABLE I

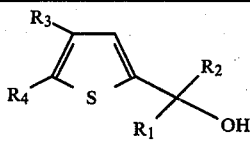

| Ex. No. | R₁ | R₂ | R₃ | R₄ | m.p.(°C.) |
|---|---|---|---|---|---|
| 1 | $CF_3$ | $CF_3$ | 4-F—phenyl | 4-F—phenyl | 75–78° |
| 2 | $CF_2Cl$ | $CFCl_2$ | 4-F—phenyl | 4-F—phenyl | *165–170° |
| 3 | $CF_3$ | $CF_3$ | 4-$CH_3O$—phenyl | 4-$CH_3O$—phenyl | 120–123° |
| 4 | $CF_3$ | $CF_3$ | 4-$CH_3O$—phenyl | 4-$CH_3S$—phenyl | 113–115° |
| 5 | $CF_3$ | $CF_3$ | 4-F—phenyl | 4-Cl—phenyl | 73–76° |
| 6 | $CF_3$ | $CF_3$ | phenyl | phenyl | oil |
| 7 | $CF_3$ | $CH_3$ | 4-F—phenyl | 4-F—phenyl | **140–150° |
| 8 | $CF_2Cl$ | $CF_2Cl$ | 4-F—phenyl | 4-F—phenyl | 78–80° |
| 9 | $CF_3$ | $CF_2H$ | 4-F—phenyl | 4-F—phenyl | 61–65° |
| 10 | $CF_3$ | $CF_2Cl$ | 4-F—phenyl | 4-F—phenyl | **130–140° |
| 11 | $CF_3$ | $CF_2Cl$ | 4-F—phenyl | 4-$CH_2S$—phenyl | |
| 12 | $CF_2Cl$ | $CF_2Cl$ | 4-F—phenyl | 4-$CH_3SO_2$—phenyl | |
| 13 | $CF_3$ | $CH_3$ | 4-F—phenyl | 4-$CH_3SO$—phenyl | |
| 14 | $CF_3$ | $CF_2Cl$ | 4-$NO_2$—phenyl | 4-F—phenyl | |
| 15 | $CF_2Cl$ | $CF_2Cl$ | 4-F—phenyl | 4-Br—phenyl | |
| 16 | $CF_3$ | $CF_3$ | 4-$CH_3$—phenyl | 4-$CH_3$—phenyl | |
| 17 | $CF_3$ | $CH_3$ | 4-F—phenyl | 4-$(CH_3)_2N$—phenyl | |
| 18 | $CF_2Cl$ | $CF_2Cl$ | phenyl | 3,4-$Cl_2$—phenyl | |
| 19 | $CF_2Cl$ | $CClFH$ | 4-F—phenyl | 4-F—phenyl | |
| 20 | $CF_3$ | $CCl_2H$ | 4-F—phenyl | 4-F—phenyl | |
| 21 | $CF_3$ | $CF_2Cl$ | 4-F—phenyl | 4-$C_2H_5S$—phenyl | |
| 22 | $CF_3$ | $CH_3$ | 4-$C_2H_5O$—phenyl | 4-F—phenyl | |
| 23 | $CF_3$ | $CF_3$ | 4-F—phenyl | Pyridyl | |
| 24 | $CF_3$ | $CF_3$ | 4-F—phenyl | 4-$CH_2S$—phenyl | |

*boiling point, (.1 mm)
**boiling point, (.05 mm)

EXAMPLE 25

Method E a. 2-Trifluoroacetyl-4,5-bis(4-fluorophenyl)thiophene

A solution of 2,3-bis(4-fluorophenyl)thiophene (10 g, 36.8 mmole) in 50 ml chloroform and 50 ml trifluoroacetic acid was treated with 10 ml trifluoroacetic anhydride and heated at reflux. After 48 hours, additional trifluoroacetic anhydride (10 ml) was added and heating continued. After twelve days total reaction time, the mixture was concentrated in vacuo. The residue was dissolved in ethyl acetate, washed with saturated aqueous $NaHCO_3$ and brine, dried and concentrated in vacuo. Recrystallization from hexanes gave the title compound (10.5 g), m.p. 120°–122°.

The proton NMR spectrum of material from a similar preparation was consistent with the assigned structure.
$^{19}F$ nmr: −72.7 ppm (s, $CF_3C(O)$), −110.9 and −113.4 ppm (2s, F-phenyl). MS 368 (M+), 299 (M—$CF_3$).

b. 4,5-Bis(4-fluorophenyl-α-ethyl-α-trifluoromethyl-2-thiophenemethanol

Magnesium turnings (660 mg, 2.5 equiv.) were covered with 9 ml dry ether and then treated with a solution of ethyl iodide (2.2 ml, 2.5 equiv.) in 5 ml ether at such a rate to maintain reflux. The reaction mixture was heated at reflux for 1 hour additional, cooled to room temperature and treated dropwise with a solution of 2-trifluoroacetyl-4,5-bis(4-fluorophenyl)thiophene (4.04 g, 11 mole) in 60 ml tetrahydrofuran. The reaction mixture was stirred 1 hour at room temperature, quenched with saturated aqueous $NH_4Cl$ and extracted with ethyl acetate. The organic extracts were washed with brine, dried and concentrated in vacuo. Chromatography on silica gel gave the title compound (0.3 g) as an oil.

Proton and fluorine NMR spectrum were consistent with the assigned structure.

MS 398 (M+), 381 (M—OH), 369 (M—$C_2H_5$), 329 (M—$CF_3$).

EXAMPLE 26 a. 2-Pentafluoropropionyl-4,5-bis(4-fluorophenyl)thiophene

1. A solution of 2,3-bis(4-fluorophenyl)thiophene (11.8 g, 43 mmole) in 50 ml toluene/250 ml ether was cooled to 5° and treated with 1.55 M n-butyl lithium (34 ml, 1.2 equiv.). The reaction mixture was heated at reflux for 1½ hours, cooled to −20° and treated dropwise with a solution of N,N-dimethylpentafluoropropionamide (10 g, 1.2 equiv.) in 15 ml ether. The reaction mixture was stirred for 3 hours at −20°, allowed to warm to 0° and then quenched with saturated aqueous $NH_4Cl$. The mixture was extracted with ethyl acetate. The organics were washed with brine, dried and concentrated in vacuo.

Chromatography on silica gel gave the title compound (3.8 g) as an oil which crystallized on standing. Recrystallization from ethanol gave product (m.p. 69°–70°). Proton NMR spectral data was consistent with the assigned structure.

2. A solution of 2-bromo-4,5-bis(4-fluorophenyl)thiophene (9.8 g, 27.9 mmole) in 200 ml tetrahydrofuran was cooled to −78° and treated dropwise with 1.55 M n-butyl lithium (22 ml, 1.2 equiv.). After 1½ hour, the reaction mixture was treated dropwise with a solution of N,N-dimethyl pentafluoropropionamide (6.4 g, 1.2 equiv.) in 15 ml tetrahydrofuran, stirred at −78° for 1½ hour, allowed to warm to 0° and quenched with water. Tetrahydrofuran was removed in vacuo and the residue partitioned between water and ethyl acetate. The organic extracts were washed with 3 N HCl, water and brine, dried and concentrated in vacuo.

Chromatography on silica gel gave the title compound (2.7 g) spectroscopically identical with material prepared in (1).

b.
4,5-Bis(4-fluorophenyl)-α-methyl-α-pentafluoroethyl-2-thiophenemethanol

A solution of 2-pentafluoropropionyl-4,5-bis(4-fluorophenyl)thiophene (5.83 g, 13.9 mmole) in 80 ml tetrahydrofuran was treated with 3 M methyl magnesium bromide (5.1 ml, 1.1 equiv.). After 3 hours, additional methyl magnesium bromide (2 ml) was added. After 4 hours total reaction time, the reaction was quenched with saturated aqueous NH₄Cl and extracted with ethyl acetate. The combined organics were washed with brine, dried and concentrated in vacuo. Chromatography on silica gel gave the title compound as an oil (4.4 g).

Infrared and proton and fluorine NMR spectra were consistent with the assigned structure.
MS 434 (M+), 417 (M—OH), 315 (M—C₂F₅).

EXAMPLE 27

Method F

3-Methyl-4,5-bis(4-fluorophenyl)-α,α-bis(chlorodifluoromethyl)-2-thiophenemethanol A solution of 2,3-dibromo-4,5-bis(4-fluorophenyl)thiophene (6.45 g, 15 mmole) in 100 ml tetrahydrofuran was cooled to −78° and treated dropwise with 1.55 M n-butyl lithium (10.6 ml, 1.1 equiv.). After 1½ hours at −78°, a solution of 1,3-dichlorotetrafluoroacetone (2.7 g, 0.9 equiv.) in 5 ml tetrahydrofuran was added followed 2¾ hours later by additional 1,3-dichlorotetrafluoroacetone (0.4 ml, 0.2 equiv.) in 2 ml tetrahydrofuran. After 4¼ hours total reaction time, the reaction mixture was treated with 1.55 M n-butyl lithium (10.6 ml, 1.1 equiv.), stirred 1 hour at −78°, treated with a solution of methyl iodide (1.1 ml, 1.1 equiv.) in 5 ml tetrahydrofuran and then allowed to warm to room temperature overnight.

The reaction mixture was quenched with water and extracted with ethyl acetate. The organic extracts were washed with brine, dried and concentrated in vacuo. Chromatography on silica gel and recrystallization from acetic acid gave the title compound (1.2 g), m.p. 83°–85°.

Fluorine and proton NMR spectra were consistent with the assigned structure.
MS 484 (M+), 399 (M—CF₂Cl).

EXAMPLE 28

Method G 4,5-Bis(4-fluorophenyl)-α,α-bis(chlorodifluoromethyl)-2-thiophenemethanol, methyl ether A solution of 4,5-bis(4-fluorophenyl)-α,α-bis(chlorodifluoromethyl)-2-thiophenemethanol (3 g, 6.4 mmole) in 50 ml dimethylformamide was treated with potassium carbonate (2.2 g, 2.5 equiv.) and methyl iodide (1 ml, 2.5 equiv.) and stirred for 4 days at room temperature. The reaction mixture was concentrated in vacuo and the residue partitioned between water and ethyl acetate. The organic extracts were washed with water and brine, dried and concentrated in vacuo. Chromatography on silica gel and crystallization from methanol gave the title compound (1.1 g), m.p. 101°–103.5°.

Fluorine and proton NMR spectra were consistent with the assigned structure.
MS 399 (M—CF₂Cl).

EXAMPLE 29

Method H 4,5-Bis(4-fluorophenyl)-α,α-bis(chlorodifluoromethyl)-2-thiophenemethanol, acetate A solution of 4,5-bis(4-fluorophenyl)-α,α-bis(chlorodifluoromethyl)-2-thiophenemethanol (3 g, 6.4 mmole) in 75 ml acetic anhydride was heated at reflux for 2 hours. Concentration in vacuo and chromatography on silica gel gave the title compound as an oil (1.8 g).

Fluorine and proton NMR spectra were consistent with the assigned structure.
MS 512 (M+), 385 (M—CF₂Cl—CH₂CO).

Examples 25–29 and other compounds which can be prepared following the procedures outlined above and illustrated in the preceding examples are summarized in Table II.

TABLE II

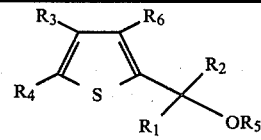

| Ex. No. | $R_1$ | $R_2$ | $R_3$ | $R_4$ | $R_5$ | $R_6$ | m.p.(°C.) |
|---|---|---|---|---|---|---|---|
| 25 | $CF_3$ | $CH_3CH_2$ | 4-F—phenyl | 4-F—phenyl | H | H | oil |
| 26 | $CH_3$ | $CF_3CF_2$ | 4-F—phenyl | 4-F—phenyl | H | H | oil |
| 27 | $CF_2Cl$ | $CF_2Cl$ | 4-F—phenyl | 4-F—phenyl | H | $CH_3$ | 83–85° |
| 28 | $CF_2Cl$ | $CF_2Cl$ | 4-F—phenyl | 4-F—phenyl | $CH_3$ | H | 101–103.5° |
| 29 | $CF_2Cl$ | $CF_2Cl$ | 4-F—phenyl | 4-F—phenyl | $CH_3CO$ | H | oil |
| 30 | $CF_3$ | $CF_3$ | 4-F—phenyl | 4-F—phenyl | $n\text{-}C_4H_9$ | H | |
| 31 | $CF_3$ | $CF_3$ | 4-F—phenyl | 4-F—phenyl | $n\text{-}C_3H_7CO$ | H | |
| 32 | $CF_3$ | $CF_2Cl$ | 4-F—phenyl | 4-F—phenyl | $CO_2CH_3$ | H | |
| 33 | $CF_2Cl$ | $CF_2Cl$ | 4-F—phenyl | 4-F—phenyl | $CO_2\text{-}n\text{-}C_4H_9$ | H | |
| 34 | $CF_2Cl$ | $CF_2Cl$ | 4-F—phenyl | 4-F—phenyl | H | $C_2H_5$ | |

DOSAGE FORMS

The anti-arthritic agents and/or analgesic agents of this invention can be administered to treat arthritis and/or alleviate pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.2 to 50, and preferably 0.5 to 25 milligrams per kilogram per day given in divided doses 2 to 4 times a day or in sustained release form is effective to obtain desired results.

Dosage forms (compositions) suitable for internal administration contain from about 1.0 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl or propyl paraben, and chlorobutanol.

Suitable pharmaceutical carriers are described in *Remington's Pharmaceutical Sciences*, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 125 milligrams of lactose, 24 milligrams of talc, and 6 milligrams magnesium stearate.

Capsules

A mixture of active ingredient in soybean oil is prepared and injected by means of a positive displacement pump into gelatin to form soft gelatin capsules containing 100 milligrams of the active ingredient. The capsules are washed in petroleum ether and dried.

Tablets

A large number of tablets are prepared by conventional procedures so that the dosage unit is 100 milligrams of active ingredient, 0.2 milligrams of colloidal silicon dioxide, 4 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized by commonly used techniques.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Pharmaceutical Utility

A procedure for detecting and comparing the antiinflammatory activity of compounds in this series and standard drugs for which there is a good correlation with human efficacy is the adjuvant-induced arthritis test in rats.

The test procedure employed for determining antiinflammatory activity is described below.

ESTABLISHED ADJUVANT-INDUCED ARTHRITIS IN RATS

Charles River Lewis male rats (130–150 grams) are injected subcutaneously in plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum Acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\text{Arthritic Control} \quad \text{Treatment Group}}{\text{Mean Paw Volume (ml)} - \text{Mean Paw Volume (ml)}} \times 100 =$$
$$\frac{}{\text{Arthritic Control} \quad \text{Non-Arthritic Control}}$$
$$\text{Mean Paw Volume (ml)} - \text{Mean Paw Volume (ml)}$$

% Decrease from Control Mean Paw Volume.

Dose-response regression lines of the % decrease are plotted on semi-log paper by visual fit and the ED50% decrease from control paw volume is determined by inspection.

TABLE II

| Compound Example No. | Results ED$_{50\%}$ Decrease From Control Paw Volume (mg/kg) |
|---|---|
| 1 | 10 |
| 4 | 10 |
| 5 | 9 |
| 6 | 21 |
| 7 | 5.5 |
| 8 | 4.5 |
| 9 | 18 |
| 10 | 6.8 |
| 27 | 12 |
| Indomethacin | 0.25 |
| Phenylbutazone | 10 |
| Aspirin | 270 |

TABLE III

| Compound Example No. | Daily Oral Dose (mg/kg) | Percent Decrease From Control Paw Volume |
|---|---|---|
| 2 | 27 | 20[1] |
| 3 | 27 | 47[2] |
| 29 | 51 | 31[2] |

[1] $p < 0.1$ compared to control by Students "t" test.
[2] $p < 0.001$ compared to control by Students "t" test.

What is claimed is:
1. A compound of the formula:

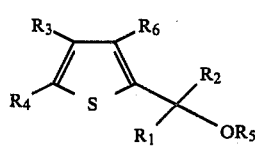

where
$R_1$ and $R_2$ independently = $CF_3$, $CF_2H$, $CFCl_2$, $CF_2Cl$, $CClFH$, $CCl_2H$, $CH_2F$, $CF_3CF_2$ or $C_1$-$C_2$ alkyl with the provisos (1) that no more than one of $R_1$ and $R_2$ can be selected from the group consisting of $CH_2F$ and $C_1$-$C_2$ alkyl and (2) that no more than one of $R_1$ and $R_2$ can be $CF_3CF_2$;
$R_3$ and $R_4$ independently = pyridyl or

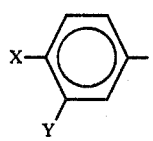

where

X=H, F, Cl, Br, $NO_2$, $C_1$-$C_2$ alkyl, $C_1$-$C_2$ alkoxy, di($C_1$-$C_2$ alkyl) amino or $C_1$-$C_2$ alkyl $S(O)_n$; where n=0, 1 or 2;
Y=H, F or Cl with the proviso that when Y is F or Cl, then X is F or Cl;
$R_5$=H, $C_1$-$C_4$ alkyl, ($C_1$-$C_3$ alkyl)C(O) or $CO_2R_7$;
$R_6$=H or $C_1$-$C_2$ alkyl; and
$R_7$=$C_1$-$C_4$ alkyl.

2. A compound of claim 1 where $R_5$ and $R_6$=H.
3. A compound of claim 2 where at least one of $R_1$ and $R_2$=$CF_3$ or $CF_2Cl$.
4. A compound of claim 2 where $R_3$ and $R_4$ independently =

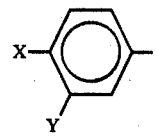

where
X=H, F, Cl, $CH_3O$, $(CH_3)_2N$, $CH_3S(O)_n$; where n=0, 1 or 2; and
Y=H.

5. A compound of claim 2 where at least one of $R_1$ and $R_2$=$CF_3$ or $CF_2Cl$; and $R_3$ and $R_4$ independently =

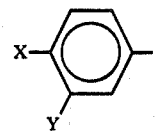

where
X=H, F, Cl, $CH_3O$, $(CH_3)_2N$, $CH_3S(O)_n$; where n=0, 1 or 2; and
Y=H.

6. A compound of claim 2 where at least one of $R_1$ and $R_2$=$CF_3$ or $CF_2Cl$; and $R_3$ and $R_4$ independently =

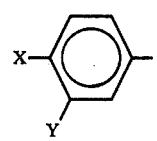

where
X=H, F, Cl, $CH_3S$, $CH_3O$; and
Y=H.

7. A compound of claim 2 where one of $R_1$ and $R_2$=$CF_3$ or $CF_2Cl$ and the other=$CH_3$, $CF_2Cl$ or $CF_3$.
8. A compound of claim 2 where $R_3$ and $R_4$ independently=

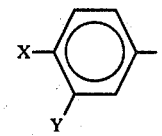

where
X=F, Cl or $CH_3S$; and

Y=H.

9. A compound of claim 2 wherein one of $R_1$ and $R_2 = CF_3$ or $CF_2Cl$ and the other $= CH_3$, $CF_2Cl$ or $CF_3$; and $R_3$ and $R_4$ independently =

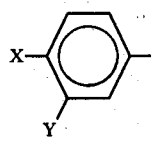

where
X=F, Cl or $CH_3S$; and
Y=H.

10. The compound of claim 1 which is 4-(4-methoxyphenyl)-5-(4-methylthiophenyl)-α,α-bis(trifluoromethyl)-2-thiophenemethanol.

11. The compound of claim 1 which is 4,5-bis(4-fluorophenyl)-α-methyl-α-trifluoromethyl-2-thiophenemethanol.

12. The compound of claim 1 which is 4,5-bis(4-fluorophenyl)-α,α-bis(trifluoromethyl)-2-thiophenemethanol.

13. The compound of claim 1 which is 5-(4-chlorophenyl)-4-(4-fluorophenyl)-α,α-bis(trifluoromethyl)-2-thiophenemethanol.

14. The compound of claim 1 which is 4,5-bis(4-fluorophenyl)-α,α-bis(chlorodifluoromethyl)-2-thiophenemethanol.

15. The compound of claim 1 which is 4,5-bis(4-fluorophenyl)-α-chlorodifluoromethyl-α-trifluoromethyl-2-thiophenemethanol.

16. A pharmaceutical composition consisting essentially of a suitable pharmaceutical carrier and an effective antiinflammatory amount of a compound of claim 1.

17. A pharmaceutical composition consisting essentially of a suitable pharmaceutical carrier and an effective antiinflammatory amount of a compound of claim 2.

18. A pharmaceutical composition consisting essentially of a suitable pharmaceutical carrier and an effective antiinflammatory amount of a compound of claim 3.

19. A pharmaceutical composition consisting essentially of a suitable pharmaceutical carrier and an effective antiinflammatory amount of a compound of claim 4.

20. A pharmaceutical composition consisting essentially of a suitable pharmaceutical carrier and an effective antiinflammatory amount of a compound of claim 5.

21. A pharmaceutical composition consisting essentially of a suitable pharmaceutical carrier and an effective antiinflammatory amount of a compound of claim 6.

22. A pharmaceutical composition consisting essentially of a suitable pharmaceutical carrier and an effective antiinflammatory amount of a compound of claim 7.

23. A pharmaceutical composition consisting essentially of a suitable pharmaceutical carrier and an effective antiinflammatory amount of a compound of claim 8.

24. A pharmaceutical composition consisting essentially of a suitable pharmaceutical carrier and an effective antiinflammatory amount of a compound of claim 9.

25. A pharmaceutical composition consisting essentially of a suitable pharmaceutical carrier and an effective antiinflammatory amount of the compound of claim 10.

26. A pharmaceutical composition consisting essentially of a suitable pharmaceutical carrier and an effective antiinflammatory amount of the compound of claim 11.

27. A pharmaceutical composition consisting essentially of a suitable pharmaceutical carrier and an effective antiinflammatory amount of the compound of claim 12.

28. A pharmaceutical composition consisting essentially of a suitable pharmaceutical carrier and an effective antiinflammatory amount of the compound of claim 13.

29. A pharmaceutical composition consisting essentially of a suitable pharmaceutical carrier and an effective antiinflammatory amount of the compound of claim 14.

30. A pharmaceutical composition consisting essentially of a suitable pharmaceutical carrier and an effective antiinflammatory amount of the compound of claim 15.

31. A method of treating inflammation in a mammal which comprises administering to the mammal an antiinflammatory amount of a compound of claim 1.

32. A method of treating inflammation in a mammal which comprises administering to the mammal an antiinflammatory amount of a compound of claim 2.

33. A method of treating inflammation in a mammal which comprises administering to the mammal an antiinflammatory amount of a compound of claim 3.

34. A method of treating inflammation in a mammal which comprises administering to the mammal an antiinflammatory amount of a compound of claim 4.

35. A method of treating inflammation in a mammal which comprises administering to the mammal an antiinflammatory amount of a compound of claim 5.

36. A method of treating inflammation in a mammal which comprises administering to the mammal an antiinflammatory amount of a compound of claim 6.

37. A method of treating inflammation in a mammal which comprises administering to the mammal an antiinflammatory amount of a compound of claim 7.

38. A method of treating inflammation in a mammal which comprises administering to the mammal an antiinflammatory amount of a compound of claim 8.

39. A method of treating inflammation in a mammal which comprises administering to the mammal an antiinflammatory amount of a compound of claim 9.

40. A method of treating inflammation in a mammal which comprises administering to the mammal an antiinflammatory amount of the compound of claim 10.

41. A method of treating inflammation in a mammal which comprises administering to the mammal an antiinflammatory amount of the compound of claim 11.

42. A method of treating inflammation in a mammal which comprises administering to the mammal an antiinflammatory amount of the compound of claim 12.

43. A method of treating inflammation in a mammal which comprises administering to the mammal an antiinflammatory amount of the compound of claim 13.

44. A method of treating inflammation in a mammal which comprises administering to the mammal an antiinflammatory amount of the compound of claim 14.

45. A method of treating inflammation in a mammal which comprises administering to the mammal an anti-inflammatory amount of the compound of claim 15.

46. A process for preparing a compound of claim 1 which comprises:

(a) contacting a compound of the formula:

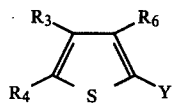

where $R_3$, $R_4$ and $R_6$ are as defined in claim 1 and Y is H or Br, with a suitable strong base or other metallating agent and then contacting the resultant intermediate with a polyhalogenated ketone $R_1C(O)R_2$ where $R_1$ and $R_2$ are as defined in claim 1; and optionally:

(b) contacting the product of step (a) with an alkylating or acylating agent.

47. A process for preparing a compound of claim 1 which comprises:

(a) contacting a compound of the formula:

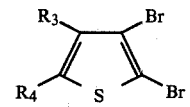

with an organometallic reagent $R_2M$ where M=Li, or MgBr where $R_1$-$R_4$ and $R_6$ are as defined in claim 1; and optionally:

(b) contacting the product of step (a) with an alkylating or acylating agent.

48. A process for preparing a compound of claim 1 which comprises:

(a) sequentially contacting a compound of the formula:

with (i) a suitable strong base or other metallating agent, (ii) a polyhalogenated ketone $R_1C(O)R_2$, (iii) a suitable strong base or other metallating agent and (iv) an alkylating reagent $R_6'L$ where $R_1$-$R_4$ are as defined in claim 1 and $R_6'$ is $C_1$-$C_2$ alkyl and L is a suitable leaving group; and optionally:

(b) contacting the product of step (a) with an alkylating or acylating agent.

* * * * *